United States Patent [19]

Benner, II et al.

[11] Patent Number: 5,015,581
[45] Date of Patent: May 14, 1991

[54] METHOD FOR PRODUCING THE HINC II RESTRICTION ENDONUCLEASE AND METHYLASE

[75] Inventors: Jack S. Benner, II, Hamilton; Phyllis A. Rees, Arlington, both of Mass.

[73] Assignee: New England Biolabs, Inc., Beverly, Mass.

[21] Appl. No.: 324,402

[22] Filed: Mar. 15, 1989

[51] Int. Cl.$^5$ .................. C12N 15/52; C12N 9/22; C12N 1/21
[52] U.S. Cl. .................. 435/172.3; 435/199; 435/252.33; 435/320.1; 536/27; 935/24; 935/73; 935/80
[58] Field of Search .................. 435/172.3, 199, 320, 435/252.3, 252.33; 935/29, 73, 80, 82; 536/27

[56] References Cited

PUBLICATIONS

Wilson, G. C. (1988), Trends in Genetics 4(11), 314–318.
Lunnen, K. D. (1988) Gene 74, 25–32.
Wilson G. C. (1988) Gene 74, 281–289.
Borck, K. (1976) Molec. Gen. Genet. 146, 199–207.
Greene, P. J. et al. (1981), J. Biol. Chem. 256(5), 2143–2153.
Newman, A. K. et al. (1981), J. Biol. Chem. 256(5), 2131–2139.
Schoner, B. et al. (1983), Gene 24, 227–236.
Walder, R. Y. et al. (1984), J. Biol. Chem. 259(12), 8015–8026.
Kessler, C. et al. (1985), Gene 33, 1, 38, 97, 99.
Mann et al., Gene 3:97–112, 1978.
Kosykh et al., Molec. Gen. Genet 178: 717–719, 1980.
Walder et al., Proc. Nat. Acad. Sci. U.S.A. 78:1503–1507, 1981.
Bougueleret et al., Nucleic Acids Res. 12:3659–3676, 1984.
Gingeras & Brooks, Proc. Natl. Acad. Sci U.S.A., 80:402–406, 1983.
Theriault & Roy, Gene 19:355–359, 1982.
Blumenthal et al., J. Bacteriol. 164:501–509, 1985.
Kiss et al., Nucleic Acids Res. 13: 6403–6421, 1985.
Szomolanyi et al. Gene 10:219–225, 1980.
Janulaitis et al., Gene 20:197–204, 1982.
Kiss & Baldauf, Gene 21:111–119, 1983.
Walder et al., J. Biol. Chem. 258: 1235–1241, 1983.
Raleigh & Wilson, Proc. Natl. Acad. Sci., U.S.A. 83:9070–9074, 1986.
Heitman & Model, J. Bact., 196:3243–3250, 1987.
Landy et al., Biochemistry 13:2134–2142, 1974.
Kelly & Smith, J. Mol. Biol., 51:393–409, 1970.
Roy & Smith, J. Mol. Biol., 81:427–459, 1973.
Smith & Wilcox, J. Mol. Biol., 51:379–391, 1970.
Birnboin & Doly, Nucleic Acids Res. 7:1513, 1979.

*Primary Examiner*—Elizabeth C. Weimar
*Assistant Examiner*—Charles L. Patterson, Jr.
*Attorney, Agent, or Firm*—Gregory D. Williams; David G. Conlin

[57] ABSTRACT

The present invention is directed to a method for cloning and producing the Hinc II restriction endonuclease by (1) introducing the restriction endonuclease gene from *Haemophilus influenzae* Rc into a host whereby the restriction gene is expressed; (2) fermenting the host which contains the vector encoding and expressing the Hinc II restriction endonuclease, and (3) purifying the Hinc II restriction endonuclease from the fermented host which contains the vector encoding and expressing the Hinc II restriction endonuclease activity.

10 Claims, 4 Drawing Sheets

Cloning the Hinc II Endonuclease

Hinc II genomic DNA was digested with Hind III pBIIHI.2 was digested with Hind III and dephosphorylated Mixed, ligated at 16oC for 24 hours and plated on media containing ampicillin Picked 300 colonies and screened on amp and amp + strep, looking for amp+strep- colonies. Over 50% were amp+strep- Grew 10.0 ml cultures of 18 colonies and did minipreps looking for clones that were resistant to digestion by Hinc II Five were resistant to Hinc II digestion, all had a 3.0kb Hind III fragment
Sonicated cells and assayed for activity on lambda DNA
Activity for clone A-10 = 2000U/gm cells Gel-prepped 3.0 kb Hind III fragment from clone A1, ligated into Hind III digested and dephosphorylated pUC19 for 24 hours at 16oC Plated on ampicillin, picked 100 colonies Grew 10.0ml cultures of 18 colonies, miniprepped and looked for resistance to digestion by Hinc II Over 50% were resistant to digestion by Hinc II, sonicated cells and assayed for activity on lambda DNA, found both orientations
Activity for 4 = 2000U/gm cells
Activity for 10 = 80,000U/gm cells

FIG. 1

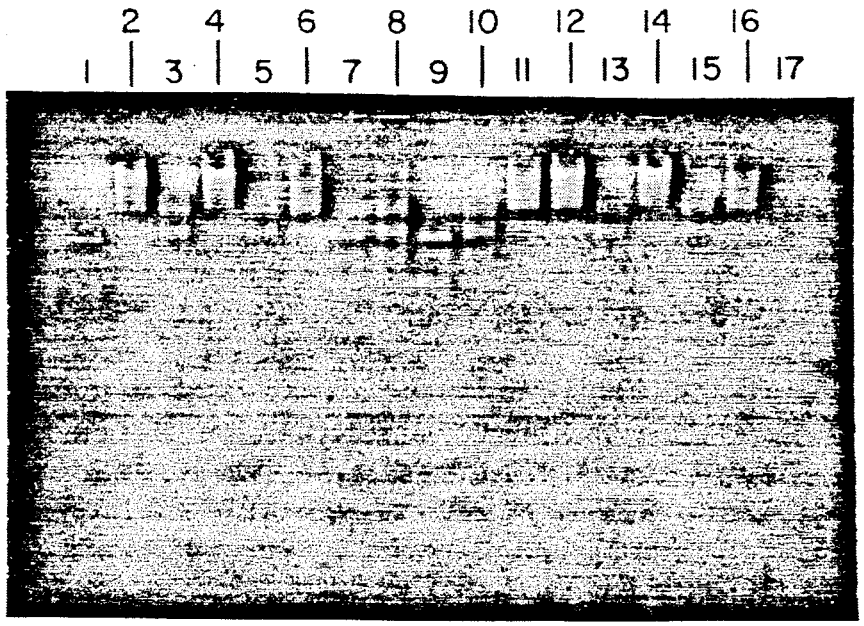

16 SEPT 88

The digests shown above are 1 ug of lambda DNA in 50 ul of restriction buffer (10mM Tris-HCl (pH7.5), 10mM MgCl2, .1M NaCl, 100ug/ml BSA) incubated for 15 minutes at 37oC with an additional component listed below for each reaction of interest:

Lane 1  1 ul Purified Hinc II Endonuclease from Haemophilus influenzae Rc cells

Lane 2  1 ul of a cell extract from E. coli strain RRI containing p(pUC19)HincIIRM-5.7-4

Lane 3  5 ul of a cell extract from E. coli strain RRI containing p(pUC19)HincIIRM-5.7-4

Lane 8  1 ul of a cell extract from E. coli strain RRI containing p(pUC19)HincIIRM-5.7-10

Lane 9  5 ul of a cell extract from E. coli strain RRI containing p(pUC19)HincIIRM-5.7-10

Figure 4

METHOD FOR PRODUCING THE HINC II RESTRICTION ENDONUCLEASE AND METHYLASE

BACKGROUND OF THE INVENTION

The present invention relates to clones for the Hinc II restriction endonuclease and modification methylase, and to the production of these enzymes from the clones.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria usually possess only a small number of restriction endonucleases per species. The endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (AT)GGCC(AT), PuGCGCPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecules and cleaving them each time that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (HhaII Mann et al., *Gene* 3: 97–112, (1978); EcoRII: Kosykh et al., *Molec. gen. Genet* 178: 717–719, (1980); PstI: Walder et al., *Proc. Nat. Acad. Sci.* USA 78 1503–1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E.coli* cloning plasmids (EcoRV: Bougueleret et al., *Nucleic Acids Res.* 12:3659–3676, (1984); PaeR7: Gingeras and Brooks, *Proc. Natl. Acad. Sci.* USA 80:402–406, (1983); Theriault and Roy, *Gene* 19:355–359, (1982); PvuII: Blumenthal et al., *J. Bacteriol.* 164:501–509, (1985)).

A third approach, and one that is being used to clone a growing number of systems, involves selecting for an active methylase gene see, e.g. EPO Publication No. 193, 413, published September 3, 1986 and (BsuRI: Kiss et al., *Nucleic Acids Res.* 13:6403–6421, (1985)). Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., *Gene* 10:219–225, (1980); BcnI: Janulaitis et al, *Gene* 20: 197–204 (1982); BsuRI: Kiss and Baldauf, *Gene* 21: 111–119, (1983); and MspI: Walder et al., *J. Biol. Chem.* 258:1235–1241, (1983)).

A potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease. Another obstacle to cloning restriction-modification systems lies in the discovery that some strains of *E. coli* react adversely to cytosine or adenine modification; they possess systems that destroy DNA containing methylated cytosine (Raleigh and Wilson, *Proc. Natl. Acad. Sci.*, USA 83:9070–9074, (1986)) or methylated adenine (Heitman and Model, *J. Bact.*, 196:3243–3250, (1987); Raleigh, Trimarchi, and Revel, *Genetics*, (in press)). Cytosine-specific or adenine-specific methylase genes cannot be cloned easily into these strains, either on their own, or together with their corresponding endonuclease genes. To avoid this problem it is necessary to use mutant strains of *E.coli* (McrA− and McrB− or Mrr−) in which these systems are defective.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention there is provided a clone containing the genes for the Hinc II restriction endonuclease and modification methylase derived from *Haemophilus influenzae* Rc (NEB strain #126, a sample of which was deposited in the ATCC under designation number 53876), as well as related methods for the production of the enzymes. More specifically, this invention relates to clones which express the restriction endonuclease Hinc II, an enzyme which recognizes the DNA sequence GTPy▼PuAC and cleaves as indicated between the first 5′ Py and Pu by the arrow. See Landy, Ruesdisueli, Robinson, and Ross, Biochemistry, 13:2134–2142, (1974); Kelly and Smith, *J. Mol. Biol.*, 51:393–409, (1970); Roy and Smith, *J. Mol. Biol.*, 81 427–444, (1973); Roy and Smith, *J. Mol. Biol.*, 81:445–459, (1973); Smith and Wilcox, *J. Mol. Biol.*, 51:379–391, (1970), the disclosure of which is hereby incorporated by reference herein.

The preferred method for cloning this enzyme comprises forming a library containing the DNA from *Haemophilus influenzae* Rc, isolating those clones which contain DNA coding for the Hinc II modification methylase and screening among these to identify those that also contain the Hinc II restriction endonuclease gene.

BRIEF DESCRIPTION OF THE DRAWINGS

FIG. 1 illustrates the scheme for cloning the Hinc II restriction endonuclease.

FIG. 4 is a photograph of an agarose gel demonstrating Hinc II restriction endonuclease activity in cell extracts of *E.coli* RR1 (ATCC 31343) carrying p(pUC19)HincIIRM-5.7-4 and p(pUC19)HincIIRM-5.7-10 (NEB #520).

DETAILED DESCRIPTION OF THE INVENTION

Figure 2:
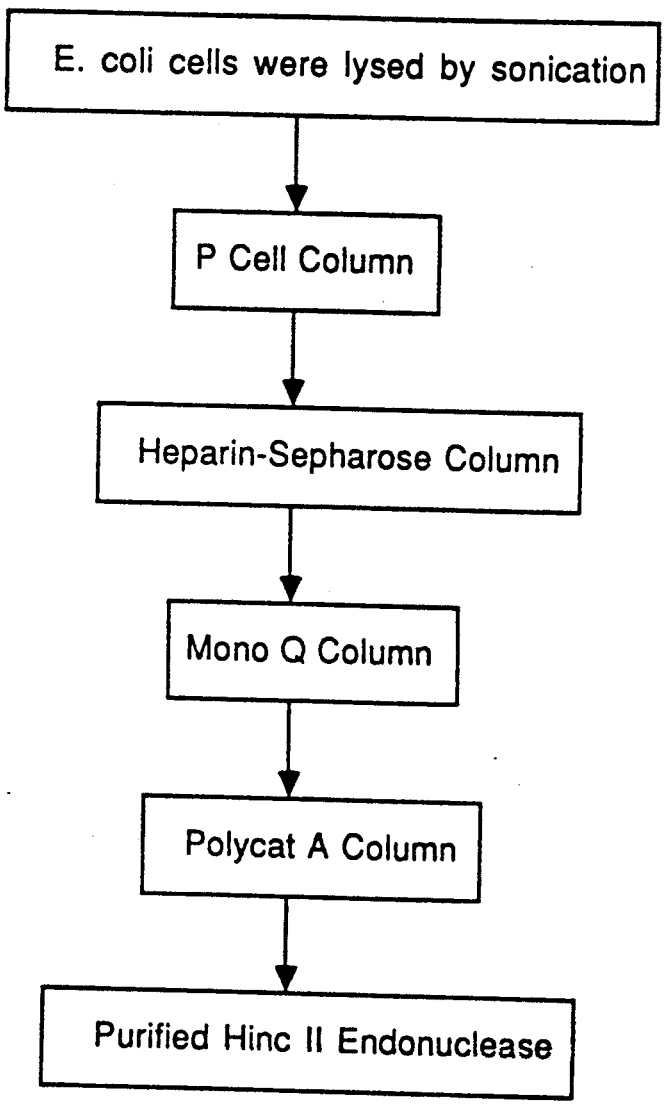
FIG. 2 illustrates the scheme for producing the Hinc II restriction endonuclease.

The present invention provides a method for cloning Hinc II restriction and modification genes and producing the restriction endonuclease Hinc II from clones produced thereby. This approach takes advantage of the fact that clones have been selected on the basis of containing expressed Hinc II restriction and methylase genes by the use of an endonuclease selection. Such clones are resistant to digestion in vitro by Hinc II restriction endonuclease.

The present invention also relates to a method for cloning the Hind II modification and restriction genes and producing the Hind II restriction endonuclease from clones produced thereby.

The methods described herein by which the Hinc II restriction gene and methylase gene are preferably cloned and expressed include the following steps:

1. The genomic DNA of *Haemophilus influenzae* Rc or *Haemophilus influenzae* Rd strains are purified.
2. The genomic DNA is digested fully with a restriction endonuclease such as Bgl II restriction endonuclease.
3. The resulting Bgl II fragments are ligated into the Bgl II cloning site of a cloning vector, such as pBIIOI (ATCC 67901) or the BamH I site of pUC19 (ATCC 37254) or pBR322 (ATCC 37017) or pACYC177 (ATCC 37031) and the mixture is used to transform an appropriate host cell such as *E. coli* RR1 cells which are mrr−.
4. The transformed mixture is plated onto media selective for transformed cells, such as the antibiotics ampicillin, tetracycline, or chloramphenicol. After incubation, the transformed colonies are collected together into a single culture, the cell library.
5. The recombinant plasmids are purified in toto from the cell library to make the plasmid library.
6. The plasmid library is digested to completion with the Hinc II restriction endonuclease, prepared from *Haemophilus influenzae* Rc by a method similar to that described in Watson et al, supra. Hinc II digestion differentially destroys unmodified, non-methylase-containing, clones, increasing the relative frequency of Hinc II methylase clones.
7. The selected DNA is transformed back into an appropriate host such as *E.coli* RR1, and transformants are recovered by plating onto selective media. The colonies are picked and their DNA is analyzed for the presence of the Hinc II modification gene: the plasmids that they carry are purified and incubated with the Hinc II restriction endonuclease to determine whether they are resistant to digestion. Total cellular DNA (chromosomal and plasmid) is also purified and incubated with the Hinc II restriction endonuclease. The DNA of clones that carry the Hinc II modification gene should be fully modified, and both plasmid DNA and total DNA should be substantially resistant to digestion.
8. The Hinc II restriction endonuclease is produced from *Haemophilus influenzae* Rc cells carrying the Hinc II restriction and modification genes. The cells are propagated in a fermenter in a rich medium containing ampicillin.
9. The cells are harvested by centrifugation.
10. The cells are disrupted by sonication to produce crude cell extract containing the Hinc II restriction endonuclease activity.
11. The crude cell extract containing the Hinc II restriction endonuclease activity is purified by standard ion-exchange and affinity chromatography techniques.
12. The endonuclease so purified will be homogeneous on SDS polyacrylmide gel electrophoresis and to have a molecular weight of 27,000 daltons and a specific activity of approximately 250,000 units/mg of protein titered on lambda DNA.

13 The amino terminal sequence of the endonuclease is obtained, and a DNA oligo probe is made based on the protein sequence.

14. The location of the endonuclease is mapped to the methylase as well as to the *Haemophilus influenzae* Rc and *Haemophilus influenzae* Rd genomes.

15. *Haemophilus influenzae* Rc genomic DNA is digested fully with a restriction endonuclease such as Hind III restriction endonuclease. *Haemophilus influenzae* Rd genomic DNA could be digested fully with a restriction endonuclease such as Cla I or EcoR I which generates fragments known to contain the Hind II modification and restriction genes.

16. The resulting Hind III fragments are ligated into the Hind III cloning site of a cloning vector, such as pBIIHI.2 (ATCC 67902) or the Hind III site of pUC19, pBR322 or pACYC177 and the mixture is used to transform an appropriate host cell such as *E. coli* RR1 cells.

17. The transformed mixture is plated onto media selective for transformed cells, such as the antibiotics ampicillin, streptomycin, or chloramphenicol. After incubation, the transformed colonies are collected together into a single culture, the cell library.

18. The recombinant plasmids are purified in toto from the cell library to make the plasmid library.

19. The plasmid library is digested to completion with the Hinc II restriction endonuclease, prepared from *Haemophilus influenzae* Rc by a method similar to that described in Watson et al, supra. Hinc II digestion differentially destroys unmodified, non-methylase-containing, clones, increasing the relative frequency of Hinc II methylase clones.

20. The selected DNA is transformed back into an appropriate host such as *E.coli* RR1, and transformants are recovered by plating onto selective media. The colonies are picked and their DNA is analyzed for the presence of the Hinc II modification gene: the plasmids that they carry are purified and incubated with the Hinc II restriction endonuclease to determine whether they are resistant to digestion. Total cellular DNA (chromosomal and plasmid) is also purified and incubated with the Hinc II restriction endonuclease. The DNA of clones that carry the Hinc II modification gene should be fully modified, and both plasmid DNA and total DNA should be substantially resistant to digestion.

21. Clones carrying the Hinc II restriction endonuclease are identified by preparing crude extracts of the clones which were determined to carry the Hinc II methylase gene, and assaying the crude extract for Hinc II restriction endonuclease activity. The level of Hinc II activity in the crude cell extract is determined to be approximately 1,000 units per gram of cells of the clone p(pBIIHI.2)HincIIRM-8.0-Al.

22. The Hind III fragment containing the methylase and endonuclease genes was subcloned into Hind III cleaved and dephosphorylated pUC19.

23. The clone containing the recombinant plasmids p(pUC19)HincIIRM-5.7-4 and p(pUC19)HincIIRM-5.7-10 which is positive for the Hinc II restriction endonuclease activity contains a single 3.0 Kb Hind III DNA fragment inserted into the Hind III cloning site of pUC19.

Figure 3:
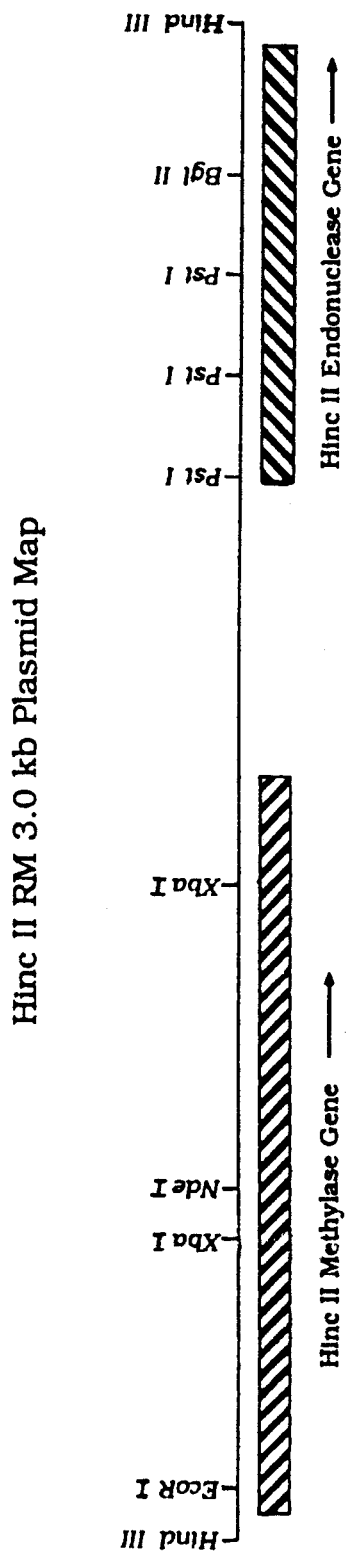
FIG. 3 is a restriction map of the 3.0 Kb Hind III fragment from *Haemophilus influenzae* Rc that encodes the Hinc II restriction endonuclease and modification methylase. The fragment was cloned into the Hind III site of pBIIHI.2 (ATCC 67902) to create p(pBIIHI.2-)HincIIRM-8.0-AI and subsequently subcloned into pUC19 (ATCC 37254) to create p(pUC19)HincIIRM-5.7-4 and p(pUC19)HincIIRM-5.7-10

24. A number of restriction endonuclease sites for various restriction endonucleases were mapped on this plasmid and are shown in FIG. 3. The positions of the genes have been determined by deletion subcloning and mapping via Southern hybridizations using DNA oligomers as probes.

25. The Hinc II restriction endonuclease is produced from cells carrying the Hinc II restriction and modification genes on the plasmid p(pUC19)HincIIRM-5.7-10. The cells are propagated in a fermenter in a rich medium containing ampicillin.

26. The cells are harvested by centrifugation.

27 The cells are disrupted by sonication to produce crude cell extract containing the Hinc II restriction endonuclease activity.

28. The crude cell extract containing the Hinc II restriction endonuclease activity is purified by standard ion-exchange and affinity chromatography techniques.

29. The endonuclease so purified is found to be homogeneous on SDS polyacrylmide gel electrophoresis and to have a molecular weight of 27,000 daltons and a specific activity of approximately 250,000 units/mg of protein titered on lambda DNA.

Although the above-outlined steps represent the preferred mode for practicing the present invention, it will be apparent to those skilled in the art that the above-described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE

Cloning of Hinc II Restriction Endonuclease Gene

1. Genomic DNA purification: Approximately five grams of *Haemophilus influenzae* Rc cells were thawed and resuspended in 0.1M Tris-HCl, pH 7.1, 0.1M ETDA (25 ml) in a Corning plastic tube (50 ml). A solution of 60 mg of lysozyme in 35 ml of the above buffer was divided into two 50 ml plastic tubes and equal portions (15 ml) of the cell suspension added to each. The solutions were incubated at 37° C. for fifteen minutes. SDS was added from a 20% stock solution to adjust the final conc. of SDS to 1%. 200 ul of a Proteinase K (20 mg/ml stock) was added and incubated for one hour at 37° C. The solution appered stringy and diffuse at this point but was not clear. Added 2 ml of 10% SDS/8% sarcosyl to the tubes (1 ml each) and heated at 55° C. for two hours. The sample remained stringy but not totally cleared. The samples were dialyzed against TE (10 mM Tris-HCl, pH 7.1, 1 mM EDTA) (2 l) with a single change - total 16 hours. After the dialysis the solution (98 ml) was prepared for CsCl gradients by dilution with an equal vol. of TE pH 8.0, divided into two portions and to each an addition of 98.0 g of CsCl and 1 ml of a 5 mg/ml Ethidium bromide was made. The twenty tubes were spun in the Ti70 rotor for 48 hrs at 44,000 rpm. The bands were removed and extracted with water saturated isobutanol. The solution was dialyzed against the same buffer (4 l) as before and then phenol and chloroform extracted (one time each). This solution was dialyzed once again to remove phenol and then subjected to electrophoresis.

2. Limit digestion: The purified DNA was cut with

Bgl II to achieve total digestion as follows: 300 ul of DNA at 100 ug/ml in 10mM Tris pH 7.5, 10 mM MgCl₂, 100 mM NaCl, 10 mM mercaptoethanol buffer was dispensed into three tubes. To the tube was added 50 units of Bgl II. The tubes were incubated at 37° C. for one hour, then phenol/chloroform extracted and ethanol precipitated. The pellets were redissolved in 300 ul of 10 mM Tris-HCl, 1 mM EDTA, pH 8.0 and 10 ul from each analyzed by agarose gel electrophoresis.

3. Ligation: The fragmented DNA was ligated to pBllOI (pBR322 with a Bgl II linker inserted into the EcoR I site) as follows: 10.0 ug of Bgl II digested *Haemophilus influenzae* Rc DNA (100 ul) was mixed with 2.0 ug of Bgl II-cleaved and dephosphorylated pBllOI (20.0 ul) and ethanol precipitated. The DNA was centrifuged at 12,000 g, 4° C. for 15 minutes and washed once with 100 ul 70% ethanol. The DNA was resuspended in 99 ul of 1X ligation buffer (50 mM Tris, pH 7.5, 10 mM MgCl₂ 10 mM DTT, 0.5 mM ATP), 1 ul of T4 DNA ligase was added and the mixture allowed to incubate at 16° C. for 16 hours. Aliquiots of 2.5 and 5.0 ul were used to transform *E. coli* strain RR1 as follows: Each aliquot was mixed with 200 ul of ice-cold competent *E. coli* RR1 cells and placed on ice for thirty minutes. After a 2-minute heat shock at 42° C., the cells were diluted with one ml of Luria-broth (L-broth) and grown for one hour at 37° C.

4. Primary Cell Library: The transformed cell cultures were centrifuged, resuspended in 250 ul volumes and plated onto Luria-agar (L-agar) plates containing 100 ug/ml ampicillin. After overnight incubation at 37° C., the plates were removed and the approximately 5000 colonies scraped-up into 25 ml of LB with antibiotic. Plasmid DNA was prepared from these cells as follows: the cells were pelleted by centrifugation and three grams of cell paste was resuspended in 14 ml of 25 mM Tris-HCl , 10 mM EDTA pH 8.0 and 50 mM glucose. The suspension was made 4.0 mg/ml in lysozyme and incubated at 25 degrees for 5 minutes. A 27 ml aliquot of 1% sodium dodecyl sulfate and 0.2 N NaOH was added followed by mixing of the solution and incubated for 5 minutes at 0 degrees. Genomic DNA was precipitated by the addition of 20 ml of ice-cold 3M potassium acetate, pH 4.8, vortexed gently for 10 seconds, left on ice for 5 minutes and centrifuged at 12,000 xg for ten minutes. The supernatant was removed and extracted with an equal volume of phenol/chloroform (1:1). The layers were separated by centrifugation at 10,000 xg for 5 minutes. The upper layer was removed and extracted with an equal volume of chloroform. The layers were separated by centrifugation at 10,000 g for 5 minutes. The upper layer was removed and the nucleic acids precipitated by the addition of two volumes of ethanol. The precipitate was collected by centrifugation at 12,000 xg for twenty minutes. The pellet was washed with 70% ethanol once and repelleted as before. The pellet was dried under vacuum and resuspended in 8 ml of 10 mM Tris-HCl, 1 mM EDTA, pH 8.0. The DNA solution was prepared for cesium chloride-ethidium bromide equilibrium density centrifugation by the addition of 8.9 grams of cesium chloride and 0.9 ml of a solution of ethidium bromide (5 mg/ml) were added. The DNA solution was centrifuged at 44,000 rpm for 48 hours and the resulting plasmid band of DNA was removed with a syringe and 18 g needle. The ethidium bromide was removed by extracting with an equal volume of CsCl-water-saturated isopropanol. The cesium chloride was removed by dialysis. The DNA was extracted with an equal volume of phenol/chloroform (1:1), and ethanol precipitated. The resultant DNA pellet was resuspended in 1.0 ml 10 mM Tris-HCl, 1 mM EDTA, pH8.0.

5. Primary Selection and Selected Library: 2 ug (30.0 ul) of the plasmid library was diluted into 60 ul of restriction endonuclease digestion buffer (10 mM Tris pH 7.5, 10 mM MgCl₂, 10 mM mercaptoethanol, 100 mM NaCl and 100 ug of bovine serum albumin). 100 units (3 ul) of Hinc II restriction endonuclease were added and the tube was incubated at 37° C. for 2 hr, at which time 7U (1 ul) of calf instentinal phosphatase was added and the reaction was incubated for an additional 30 minutes. Aliquots of this reaction mixture, 2 ul and 4 ul, were mixed with 200 ul of ice-cold competent *E. coli* RR1 cells and transformed, plated and grown overnight as for the primary library.

6. Analysis of individuals: Colonies from the above transformation were picked and plated on LB agar plates containing ampicillin and tetracycline. Eighteen colonies, which were amp$^R$ and tet$^R$ were grown up in 10 ml cultures and the plasmids that they carried were prepared by the following miniprep purification procedure, adapted from the method of Birnboim and Doly (Nucleic Acids Res. 7: 1513 (1979)).

Miniprep Procedure: Each culture was processed as follows: The 1.5 ml overnight culture was pelleted at 6,000 xg for 5 minutes. The supernatant was poured off and the cell pellet was resuspended in 150 ul of 25 mM Tris, 10 mM EDTA, 50 mM glucose, pH 8.0, containing 1 mg/ml lysozyme. After five minutes at room temperature, 200 ul of 0.2M NaOH, 1% SDS was added and the tube was shaken to lyse the cells, then placed on ice. After five minutes, 150 ul of 3M sodium acetate, pH 4.8, was added and shaken and placed on ice for an additional five minutes. The precipitate that formed was spun down at 12,000 xg, 4° C. for 10 minutes. The supernantant was removed and extracted with an equal volume of phenol/chloroform (1:1). The layers were separated by centrifugation at 10,000 xg for five minutes. The supernatant was poured into a centrifuge tube containing 880 ul of ethanol and mixed. After 10 minutes at room temperature, the tube was spun at 12,000 xg for 10 minutes to pellet the precipitated nucleic acids. The supernatant was discarded and the pellet was washed again with one ml of 70% ethanol-water, repelleted and dried at room temperature for 30 minutes under vacuum. Once dry, the pellet was resuspended in 50 ul of 10 mM Tris, 1 mM EDTA, pH 8 0 containing 20 ug/ml RNase and incubated for 1 hour at 37° C. to digest the RNA.

The plasmid minipreps were subsequently analyzed by digestion with Hinc II and Bgl II.

7. Methylase Gene Clones: 10% of the plasmids that were analyzed were found to be resistant to Hinc II and to carry a Bgl II fragment of approximately 6.2 Kb in length. These plasmids were subsequently shown to carry only the Hinc II modification methylase gene and not the restriction endonuclease gene. The other 90% of the plasmids looked at were not resistant to Hinc II and contained spurious fragments or were vector religated.

8. Restriction Gene Clones: The clones identified above (section 7) as carrying the Hinc II modification methylase gene were also tested for the Hinc II restriction endonuclease gene. This was performed as follows: The remaining portion of the overnight culture was used to check for endonuclease activity. This was done as follows:

Endonuclease Assays:

10× restriction endonuclease-buffer: 100 mM Tris, pH 7.5, 100 mM MgCl₂, 100 mM 2-mercaptoethanol, 1M NaCl.

Cell extracts were prepared as follows: Cells from one ml were pelleted by centrifugation at 4,000 rpm for five minutes. The supernatant was discarded and the pellet was resuspended in one ml of sonication buffer (10 mM Tris, pH 7.5, 100 mM NaCl, 5 mM DTT, 0.1 mM EDTA) and sonicated gently for two 10-second bursts to disrupt the cells. The tube was spun for ten minutes in a microfuge at 4° C., and the supernatant was used as the cell extract. The extract, 1 ul and 5 ul, were incubated with one ug of lambda DNA in 50 ul of 1× restriction endonuclease buffer for fifteen minutes at 37° C. Neither of the clones tested had endonuclease activity.

9. Hinc II endonuclease from *Haemophilus influenzae* Rc designated NEB#126 was propagated in a fermenter at 37 degrees C. in TRY-YE Broth medium consisting of: tryptone, 10.0 g per liter; yeast extract, 5.0 g per liter; NaCl, 2.0 g per liter; K₂HPO₄, 4.4 g per liter; glucose, 2.0 g per liter; hemin bovine, 10 mg per liter; NAD;DPN, 2.0 mg per liter. The cells are collected by centrifugation and the cell paste is used fresh or stored at −70° C.

10. All subsequent steps are carried out at 4° C.

11. The cell paste (200 grams) is thawed and the cells are resuspended in 400 mls sonication buffer (20 mM K₂PO₄, pH7.3, 0.1 mM EDTA, 10 mM B-mercaptoethanol, .0.1M NaCl).

12. The cells are disrupted by sonication (250 watts for two minutes, cooled on ice for five minutes, three times), to achieve release of approximately 50 mg of soluble protein per ml of suspended cells.

13. The insoluble cell debris is removed by centrifugation at 21,000× g for 20 minutes.

14. The supernatant fluid is applied to a phosphocellulose column (5×35 cm) (Whatman P-11) equilibrated with 20 mM KH₂PO₄, pH 6.9, 100 mM NaCl, and 10 mM 2-mercaptoethanol. The column is washed with two column volumes of the above buffer. The flow-though from the column is collected in a single flask. Hinc II endonuclease is retained by the column and elutes between 0 3 and 0.6M NaCl. The most active fractions are pooled and dialyzed against 20mM K₂PO₄, pH7.3, 0.1 mM EDTA, 10 mM B-mercaptoethanol, 0.1M KCl.

15. The pool from the phosphocellulose column is applied to a Heparin-Sepharose CL-6B column (2.5×25 cm) equilibrated with 20 mM K₂PO₄, pH 7.4, 0.1 mM EDTA, 10 mM B-mercaptoethanol, 0.1M KCl and washed with two column volumes of the same buffer. A linear gradient of KCl from 0.1M to 1.0M (total volume 700 ml) is developed and applied to the column. Ten ml fractions are collected. The fractions are assayed for the presence of the Hinc II restriction endonuclease activity on lambda DNA. The active fractions are pooled and dialysed against 100 volumes of buffer (20 mM K₂PO₄, pH7.3 0.1 mM EDTA, 10 mM B-mercaptoethanol, 0.1M KCl.

16. The dialyzed pool (50 ml) of Hinc II activity is applied to a 1 ml Mono Q FPLC column (Pharmacia) and washed with buffer S (20 mM K₂PO₄, pH6.9 10 mM B-mercaptoethanol, 0.05M KCl and a 40 ml linear gradient from 50 mM KCl to 01.0 M KCl is developed in S buffer and applied to the column. One ml fractions are collected and assayed for the presence of Hinc II restriction endonuclease activity.

17. The center fractions containing the majority of Hinc II activity are applied to a 1 ml Poly Cat-A FPLC column (Pharmacia) and washed with buffer S (20 mM K₂PO₄, pH6.9 10 mM B-mercaptoethanol, 0.05M KCl and a 40 ml linear gradient from 50 mM KCl to 01 0 M KCl is developed in S buffer and applied to the column. One ml fractions are collected and assayed for the presence of Hinc II restriction endonuclease activity. The two most active fractions are homogeneous. The endonuclease was found to have a specific activity of approximately 250,000 units/mg protein and a molecular weight on SDS-polyacrylamide gels of 27,000 Daltons.

18. 10 ug of the homogeneous Hinc II endonuclease was subjected to amino terminal protein sequencing on an Applied Biosystems Model 470A gas phase protein sequencer. The first 24 residues were degraded. The sequence obtained was the following: X F I K P I X Q D I N X X L I G Q K V K X X K X (refer to Table 1 for explanation of 1 letter code for protein sequence).

19. Based on the protein sequence, a 14-mer oligomer was made with the following sequence: 5' ATH GGN CAR AAA GT 3' (H =A, C, or T; N=A, C, G, or T; R=A or G) which was used to map the location of the amino terminal end of the endonuclease on p(pBIIOI)-HincM-10.5-1. This oligomer was also used to obtain DNA sequence which verified the protein sequence and was used to have a sequence specific 25-mer oligomer made with the following sequence: 5' ATG AGT TTC ATA AAA CCT ATT TAT C 3'. Using this 25-mer oligomer, DNA sequence was obtained that helped to determine the direction of the endonuclease and further defined the location of the amino terminal end of the endonuclease as well as the portion of the endonuclease gene that was present in p(pBIIOI)HincM-10 5-1. The DNA sequence obtained was the following: 5' TAC TCA AAG TAT TTT GGA TAA ATA GTC CTA TAA TTG NNA ATA TTA ATC GGG CAA AAA GTG AAA CGT CCT AAA TCA GGT ACT CTG TCA GGT CAT GCT GCA GGG GAA CCA TTT GAA AAA TTA GTA TAT AAG TTT TTG AAA GAA AAC CTG TCA GAT TTA ACA TTT AAG CAA TAT GAA TAT CTT AAT GAT TTA TTT ATG AAG AAC CCT GCG ATA ATT GAG CAT G 3'. The 25-mer oligomer was also used to map the endonuclease gene to various restriction fragments of the *Haemophilus inflenzae* Rc genome. With the use of a sequence specific oligomer made to the vector DNA, and a deletion clone known to be located within the methylase gene, the direction of the methylase gene was determined in the same manner that the direction of the endonuclease gene was determined.

20. Based on the data obtained in step 18, purified *Haemophilus influenzae* Rc genomic DNA (prepared as in step 1) was subjected to a limit digestion using Hind III as follows: 300 ul of DNA at 100 ug/ml in 10 mM Tris pH 7.5, 10 mM MgCl₂, 100 mM NaCl, 10 mM mercaptoethanol buffer was dispensed into one tube. To the tube was added 50 units of Hind III. The tubes were incubated at 37° C. for one hour, then phenol/chloroform extracted and ethanol precipitated. The pellets were redissolved in 300 ul of 10 mM Tris-HCl, 1 mM EDTA, pH 8.0 and 10 ul from each analyzed by agarose gel electrophoresis.

21. Ligation: The fragmented DNA was ligated to pBIIHI.2 (pN01523, with a Hpa I linker inserted into the Pvu II site and a Bgl II linker inserted into the EcoR I site) as follows: 10.0 ug of Hind III digested Haemophilus influenzae Rc DNA (100 ul) was mixed with 2.0 ug of Hind III-cleaved and dephosphorylated pBIIHI.2 (20.0 ul) and ethanol precipitated. The DNA was centrifuged at 12,000 g, 4° C. for 15 minutes and washed once with 100 ul 70% ethanol. The DNA was resuspended in 99 ul of 1× ligation buffer (50 mM Tris, pH 7.5, 10 mM MgCl$_2$ 10 mM DTT, 0.5 mM ATP), 1 ul of T4 DNA ligase was added and the mixture allowed to incubate at 16° C. for 16 hours. Aliquots of 2.5 and 5.0 ul were used to transform E. coli strain RR1 as follows: Each aliquot was mixed with 200 ul of ice-cold competent E. coli RR1 cells and placed on ice for thirty minutes. After a 2-minute heat shock at 42° C., the cells were diluted with one ml of Luria-broth (L-broth) and grown for one hour at 37° C.

22. Primary Cell Library: Prepared as in step 4 with one additional step: based on the data obtained from step 18, the libraries were probed with the sequence specific 25-mer oligomer (step 19), looking for a Hind III fragment of the appropriate size which was presumed to contain the endonuclease and methylase This fragment was present in the primary cell library.

23. Primary Selection and Selected Library: Prepared as in step 5.

24. Analysis of individuals: Colonies from the above transformation were picked and plated on LB agar plates containing ampicillin and LB agar plates containing ampicillin and streptomycin. Eighteen colonies, which were amp$^R$ and strep$^S$ were grown up in 10 ml cultures and the plasmids that they carried were prepared by the miniprep purification procedure described in step 6. The plasmid minipreps were subsequently analyzed by digestion with Hinc II and Hind III.

25. Methylase Gene Clones: 27% of the plasmids that were analyzed were found to be resistant to Hinc II and to carry a Hind III fragment of approximately 3.0 Kb in length. These plasmids were subsequently shown to carry both the Hinc II modification methylase and restriction endonuclease genes. These plasmids were also found to each carry one or more spurious fragments. The other 73% of the plasmids looked at were not resistant to Hinc II and either contained spurious fragments or were vector religated.

26. Restriction Gene Clones: The clones identified above (section 24) as carrying the Hinc II modification methylase gene were also tested for the Hinc II restriction endonuclease gene. This was performed as described in step 8. All of the clones tested had endonuclease activity.

27. All methylase positive clones were found to contain endonuclease. These clones were found to synthesize about 1,000 units of Hinc II restriction endonuclease per gram of wet cell paste in either orientation.

28 p(pBIIHI.2)HincIIRM-8.0-AI was used to transform an isogenic series of E. coli strains, looking for potential effects caused by either the Mcr A, Mcr B or mrr phenotypes. It was discovered that this RM clone was unable to transform, and hence be propagated, in any mrr+ strains.

29. The 3.0 kb Hind III fragment from p(pBIIHI.2-)HincIIRM-8.0-Al was gel prepped and used in a ligation reaction with Hind III cut and dephosphorylated pUC 19 in the following manner: 250 ng of the 2.7 kb gel prepped fragment (20 ul) was mixed with 100 ng (1 ul) of Hind III cut and dephosphorylated pUC 19 and ethanol precipitated. The DNA was centrifuged at 12,000 g, 4° C. for 15 minutes and washed once with 100ul 70% ethanol. The DNA was resuspended in 10 ul of 1X ligation buffer (50 mM Tris, pH 7.5, 10 mM MgCl$_2$ 10 mM DTT, 0.5 mM ATP), 1 ul of T4 DNA ligase was added and the mixture allowed to incubate at 16° C. for 16 hours. An liquots of 5.0 ul was used to transform E. coli strain RR1 as follows: Each aliquot was mixed with 200 ul of ice-cold competent E. coli RR1 cells and placed on ice for thirty minutes. After a 2-minute heat shock at 42° C., the cells were diluted with one ml of Luria-broth (L-broth) and grown for one hour at 37° C. The transformed cell cultures were centrifuged, resuspended in 250 ul volumes and plated onto Luria-agar (L-agar) plates containing 100 ug/ml ampicillin. After overnight incubation at 37° C., colonies were picked and plated onto LB agar containing ampicillin and incubated overnight at 37° C. Eighteen colonies, which were amp$^R$ were grown up in 10 ml cultures and the plasmids that they carried were prepared by the miniprep purification procedure described in step 6. The plasmid minipreps were subsequently analyzed by digestion with Hinc II and Hind III.

30. Methylase Gene Clones: Over 50% of the plasmids that were analyzed were found to be resistant to Hinc II digestion and to carry a Hind III fragment of approximately 3.0 Kb in length. These plasmids were subsequently shown to carry both the Hinc II modification methylase and restriction endonuclease genes. The remainder of the plasmids were pUC19 religated.

31. Restriction Gene Clones: The clones identified above (section 28) as carrying the Hinc II modification methylase gene were also tested for the Hinc II restriction endonuclease gene. This was performed as described in step 8. All of the clones tested had endonuclease activity.

32. All methylase positive clones were found to contain endonuclease. These clones were found to synthesize about 80,000 units of Hinc II restriction endonuclease per gram of wet cell paste in orientation A, p(pUC19)HincIIRM-5.7-10 (NEB #520), and 2,000 units of Hinc II restriction endonuclease per gram of wet cell paste in orientation B, p(pUC19)HincIIRM-5.7-4.

33. The recombinant plasmid p(pUC)HincIIRM-10-5.7 (NEB #520) which carries the genes encoding the Hinc II restriction endonuclease and methylase was transferred to E coli strain RR1 by transformation, a sample of which has been deposited at the American Type Culture Collection under ATCC Accession No. 40896. In transforming the same isogenic series of strains as in step 27, p(pUC)HincIIRM-10-5.7 (NEB #520) was able to tranform into these strains, but was unable to be propagated in liquid cultures larger then 10 ml.

34. Hinc II endonuclease was prepared as described in steps 9-16 with one alteration, the cells were grown in LB broth medium consisting of: 10 grams per liter, casein hydrolysate; 5 grams per liter, yeast extract; 10 grams per liter, NaCl; 1 gram per liter, magnesium chloride-hexahydrate; 1 gram per liter, glucose; 100 mg per liter ampicillin. The pH is adjusted to 7.2 with NaOH. The endonuclease purified was found to have a specific activity of approximately 250,000 units/mg protein.

TABLE 1

Amino Acid Sequence to mRNA (DNA) Sequence

TABLE 1-continued

| 1 letter code | G | A | V | L | I | S | T | D | N | E | Q | K | P | H |
|---|---|---|---|---|---|---|---|---|---|---|---|---|---|---|
| 3 letter code | Gly | Ala | Val | Leu | Ile | Ser | Thr | Asp | Asn | Glu | Gln | Lys | Pro | His |
| mRNA 5' | GGA | GCA | GUA | CUA | AUA | UCA | ACA | GAC | AAC | GAA | CAA | AAA | CCA | CAC |
| | C | C | C | C | C | C | C | U | U | G | G | G | C | U |
| | G | G | G | G | U | G | G | | | | | | G | |
| | U | U | U | U | | U | U | | | | | | U | |
| | | | | or | | or | | | | | | | | |
| | | | | UUA | | AGC | | | | | | | | |
| | | | | G | | U | | | | | | | | |

| 1 letter code | R | F | Y | W | C | M |
|---|---|---|---|---|---|---|
| 3 letter code | Arg | Phe | Tyr | Trp | Cys | Met |
| mRNA 5' | CGA | UUC | UAC | UGG | UGC | AUG 3' |
| | C | U | U | | C | |
| | G | | | | | |
| | U | | | | | |
| | or | | | | | |
| | AGA | | | | | |
| | G | | | | | |

Special Signals  RNA
UAA = Ochre            Amino Acid Special Symbols  B = D or N
UAG = Amber                                        Z = E or Q
UGA = terminate Ambiguous nucleotide abbreviations
These abbreviations conform to the proposed IUPAC-IUB standard abbreviations.

|       | A | C | G | U/T |                |
|-------|---|---|---|-----|----------------|
| U/T = |   |   |   | U   | Uracil/Thymine |
| G =   |   |   | G |     | Guanine        |
| K =   |   |   | G | U   |                |
| C =   |   | C |   |     | Cytosine       |
| Y =   |   | C |   | U   | Pyrimidine     |
| S =   |   | C | G |     |                |
| B =   |   | C | G | U   |                |
| A =   | A |   |   |     | Adenine        |
| W =   | A |   |   | U   |                |
| R =   | A |   | G |     | Purine         |
| D =   | A |   | G | U   |                |
| M =   | A | C |   |     |                |
| H =   | A | C |   | U   |                |
| V =   | A | C | G |     |                |
| N/X = | A | C | G | U   |                |

What is claimed is:

1. Isolated DNA coding for the HincII restriction endonuclease, wherein the isolated DNA is obtainable from the vector p(pUC)HincIIRM-10-5.7.

2. A recombinant DNA vector comprising a vector into which a DNA segment coding for the HincII endonuclease produced by Haemophilus influenza Rc ATCC No. 53876 has been inserted.

3. Isolated DNA coding for the HincII restriction endonuclease and methylase, wherein the isolated DNA is obtainable from the vector p(pUC)HincIIRM-10-5.7.

4. A cloning vector which comprises the isolated DNA of claim 3.

5. The cloning vector of claim 4, wherein the cloning vector comprises p(pUC)HincIIRM-10-5.7.

6. A host cell transformed by the vector of claim 2, 4 or 5.

7. A method of producing HincII restriction endonuclease comprising culturing a host cell transformed with the vector of claim 2, 4 or 5 under conditions suitable for the expression of said endonuclease.

8. A method of cloning a HincII restriction endonuclease gene which comprises:
   (a) forming a library from plasmid DNA from *Haemophilus influenza* Rc obtainable from ATCC No. 53876 by digesting said plasmid DNA with Bgl II;
   (b) contacting the plasmid library of step (a) with Hinc II to form a digestion pool, transforming the digestion pool into a host cell, and screening for cloning vectors which contain DNA coding for the HincII methylase;
   (c) purifying HincII restriction-endonuclease from the *Haemophilius influenza* Rc of step (a), partially sequencing the endonuclease and forming a DNA probe based on the partial amino acid sequence of the endonuclease;
   (d) determining the direction and location of DNA coding for the endonuclease by contacting the probe of step (c) with the cloning vectors of step (b) containing DNA coding for the HincII methylase;
   (e) from the direction and location of the DNA coding for the endonuclease determined in step (d), forming a library which contains DNA coding for the HincII endonuclease; and
   (f) isolating one or more cloning vectors of step (e) which contain DNA coding for the HincII endonuclease.

9. A method for producing HincII restriction endonuclease comprising culturing a host cell transformed with the cloning vector of claim 8, step (f) under conditions suitable for expression of said endonuclease.

10. The isolated DNA of claim 1 or 3, wherein the isolated DNA includes the DNA sequence: 5' TAC TCA AAG TAT TTT GGA TAA ATA GTC CTA TAA TTG NNA ATA TTA ATC GGG CAA AAA GTG AAA CGT CCT AAA TCA GGT ACT CTG TCA GGT CAT GCT GCA GGG GAA CCA TTT GAA AAA TTA GTA TAT AAG TTT TTG AAA GAA AAC CTG TCA GAT TTA ACA TTT AAG CAA TAT GAA TAT CTT AAT GAT TTA TTT ATG AAG AAC CCT GCG ATA ATT GAG CAT G 3'.

* * * * *